(12) United States Patent
Walde

(10) Patent No.: US 6,300,754 B1
(45) Date of Patent: Oct. 9, 2001

(54) CIRCUIT FOR AN NOX MEASUREMENT SENSOR

(75) Inventor: Tim Walde, Regensburg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/511,817

(22) Filed: Feb. 24, 2000

(30) Foreign Application Priority Data

Feb. 24, 1999 (DE) ................................................ 199 07 946

(51) Int. Cl.$^7$ ....................................................... G01N 27/00
(52) U.S. Cl. ........................ 324/71.1; 324/425; 324/378; 204/424
(58) Field of Search ..................................... 324/425, 439, 324/444, 71.1, 378; 204/424, 425, 426; 205/781

(56) References Cited

U.S. PATENT DOCUMENTS 6,214,207 * 4/2001 Miyata et al. ........................ 205/781

OTHER PUBLICATIONS

"Thick Film ZrO2 NOx Sensor for the Measurement of Low NOx Concentration", Nobuhide Kato et al., Society of Automotive Engineers, 1998, pp. 69–77.

"Performance of Thick Film NOx Sensor on Diesel and Gasoline Engines", Nobuhide Kato et al., Society of Automotive Engineers, 1997, pp. 199–206.

* cited by examiner

Primary Examiner—Safet Metjahic
Assistant Examiner—E P LeRoux
(74) Attorney, Agent, or Firm—Herbert L. Lerner; Laurence A. Greenberg; Werner H. Stemer

(57) ABSTRACT

The pump currents in an NOx measurement sensor are generated by voltage-controlled current sources. Instead of the respective pump current, a setting voltage received by the voltage-controlled current sources occurs as the feedback variable in a respective control loop, so that a current measurement can be dispensed with.

18 Claims, 3 Drawing Sheets

CIRCUIT FOR AN NOX MEASUREMENT SENSOR

BACKGROUND OF THE INVENTION

FIELD OF THE INVENTION

The invention relates to a circuit for an NOx measurement sensor.

In order to measure the NOx concentration in a gas, for example in the exhaust gas of an internal combustion engine, it is known to employ a thick-layer measurement sensor. Such a measurement sensor is described, for example, in the publication by N. Kato et al., titled "Thick Film $ZrO_2$ NOx Sensor for the Measurement of Low NOx Concentration", Society of Automotive Engineers, Publication Number 980170, 1989, or in the publication by N. Kato et al., titled "Performance of Thick Film NOx Sensor on Diesel and Gasoline Engines", Society of Automotive Engineers, Publication Number 970858, 1997. The measurement sensor has two measurement cells and is composed of a zirconium oxide that conducts oxygen ions. It implements the following measurement concept: in a first measurement cell, to which the gas to be measured is fed via a diffusion barrier, a first oxygen concentration is established by use of a first oxygen ion pump current, the intention being that no decomposition of NOx takes place. In a second measurement cell, which is connected to the first via a diffusion barrier, the oxygen content is lowered further by use of a second oxygen ion pump current. The decomposition of NOx at a measurement electrode leads to a third oxygen ion pump current, which is a measure of the NOx concentration. The entire measurement sensor is in this case brought to an elevated temperature, for example 750° C., by an electric heater.

In order to measure the third pump current, representing the measure of the NOx concentration, the current is normally fed through a measurement resistor, and the voltage drop across the resistor is tapped off and measured. In order to achieve the required accuracy, this measurement has to be carried out with a relatively high resolution. If it were wished to use a microcontroller that is normally employed for such measurement tasks, it has been shown that an analog/digital converter with a resolution of 8 bits is not adequate for this. The difficulties of current measurement are therefore to be seen essentially in the necessary resolution of the analog/digital converter and in measurement errors in the converter (offset, gain, etc.). It is therefore necessary to employ more expensive microcontrollers, of which only a few models are available on the market, so that the choice for the production or configuration is restricted here.

SUMMARY OF THE INVENTION

It is accordingly an object of the invention to provide a circuit for an NOx measurement sensor which overcomes the above-mentioned disadvantages of the prior art devices of this general type.

With the foregoing and other objects in view there is provided, in accordance with the invention, a circuit for a measurement sensor that registers an NOx concentration in a gas, the measurement sensor having an external electrode to be exposed to the gas to be measured, measurement cells including a first measurement cell and a second measurement cell connected to the first measurement cell, a measurement electrode disposed in the second measurement cell, a reference electrode exposed to ambient air, a solid-state electrolyte having the measurement cells disposed therein and the measurement electrode and the reference electrode making contact with the solid-state electrolyte, the circuit containing:

a first circuit configuration for establishing in the first measurement cell an oxygen concentration differing from an oxygen concentration in the gas to be measured;

a second circuit configuration for establishing in the second measurement cell an oxygen concentration differing from the oxygen concentration in the first measurement cell; and a third circuit configuration for pumping oxygen ions formed from NOx out of the second measurement cell from the measurement electrode to the external electrode in a pump current, the third circuit configuration including:

a controller connected to the measurement electrode and the reference electrode and generating a setting voltage; and a voltage-controlled current source for driving the pump current and receiving the setting voltage generated by the controller, the controller taping off a Nernst voltage between the measurement electrode and the reference electrode and regulating the setting voltage such that a predicted Nernst voltage is established, a value of the setting voltage being a measure of the pump current and consequently of the NOx concentration to be measured.

According to the invention, the measurement of the pump current itself is entirely dispensed with. Instead, the circuit according to the invention provides a voltage-controlled current source that drives the pump current in question. The measurement signal which is registered is then no longer the driven current but the setting voltage of the voltage-controlled current source. Since the setting voltage is predefined directly by a controller, for example a microcontroller, it no longer has to be measured, but is defined by the microcontroller and is therefore known to the latter.

The use of the voltage-controlled current source therefore has a number of advantages: the measurement of the pump current, which is normally needed in each circuit configuration, via a measurement resistor and a suitable voltage tap, can therefore be dispensed with. Normally, an analog/digital port on a microcontroller would have to be employed to measure each pump current. Furthermore, the analog/digital port would have to have a high resolution, in order to be able to measure the current with sufficient accuracy. The fact that the current measurement is dispensed with and the known setting voltage occurs in its place results in that an 8-bit microcontroller, which is more cost-effective and available in many models, can be employed.

Also dispensed with are any measurement errors in the determination of the pump currents.

It is advantageous that all the pump currents which have to be driven in order to operate the NOx measurement sensor are generated by the voltage-controlled current source whose setting voltage is predefined by the controller, so that the measurement of all the currents can be dispensed with.

In an advantageous refinement, the setting voltage is generated by the microcontroller from a pulse-width-modulated signal, which is applied to a switching transistor which connects a reference circuit to a low-pass filter which, from the signal, uses the pulse duty factor of the pulse-width-modulated signal to provide a proportional output voltage, which serves as the setting voltage.

Finally, the driven pump current is independent of the impedance of the pump current circuit and is determined only by, for example, the known and accurate pulse duty factor of the pulse-width-modulated signal from the microcontroller.

Other features which are considered as characteristic for the invention are set forth in the appended claims.

Although the invention is illustrated and described herein as embodied in a circuit for an NOx measurement sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
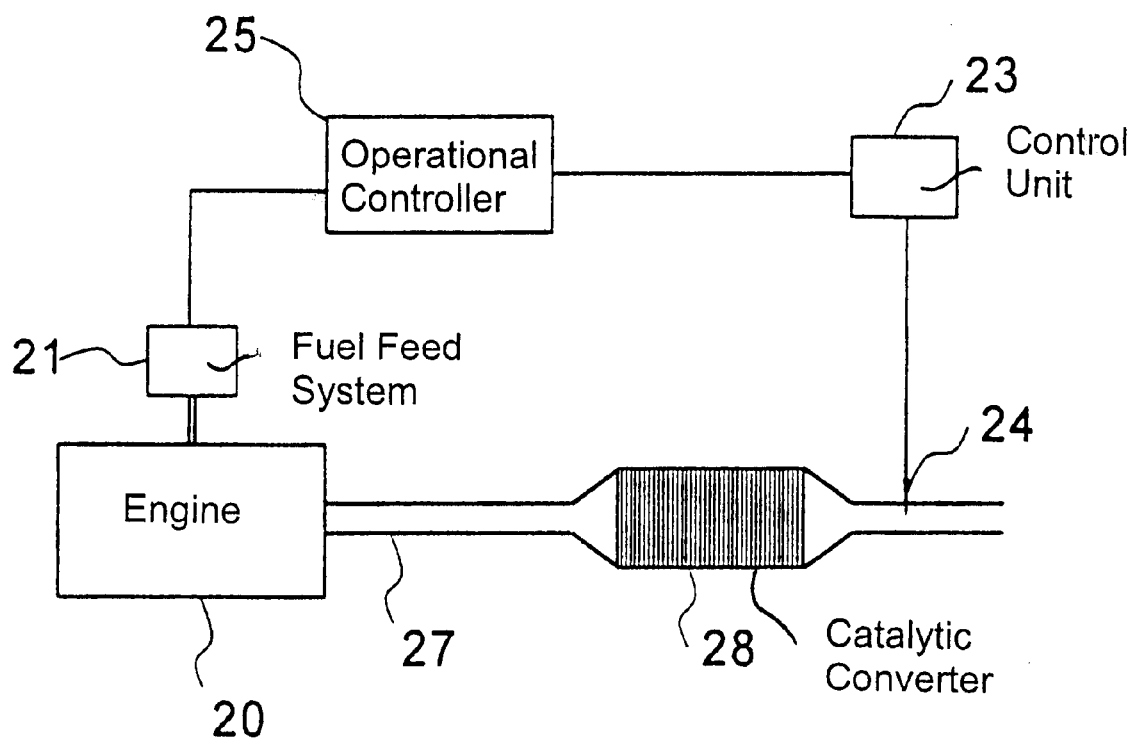
FIG. 1 is a block diagram of an internal combustion engine, in which an NOx measurement sensor with a circuit according to the invention can be used.

In all the figures of the drawing, sub-features and integral parts that correspond to one another bear the same reference symbol in each case. Referring now to the figures of the drawing in detail and first, particularly, to FIG. 2 thereof, there is shown a section through an NOx measurement sensor 1 in schematic form. The measurement sensor 1 is employed in an apparatus illustrated in FIG. 1 as a measurement sensor 24 for determining an NOx concentration in an exhaust-gas tract 27 of an internal combustion engine 20. To this end, measured values from the NOx measurement sensor 24 are read by a control unit 23, which is connected to the NOx measurement sensor 24, and are fed to an operational controller 25 of the internal combustion engine 20. The operational controller 25 drives a fuel feed system 21 of the internal combustion engine in such a way that an NOx-reducing catalytic converter 28, which in this case is located upstream of the NOx measurement sensor 24 in the exhaust-gas tract 27 of the internal combustion engine 20, exhibits optimum operating behavior.

Figure 2:
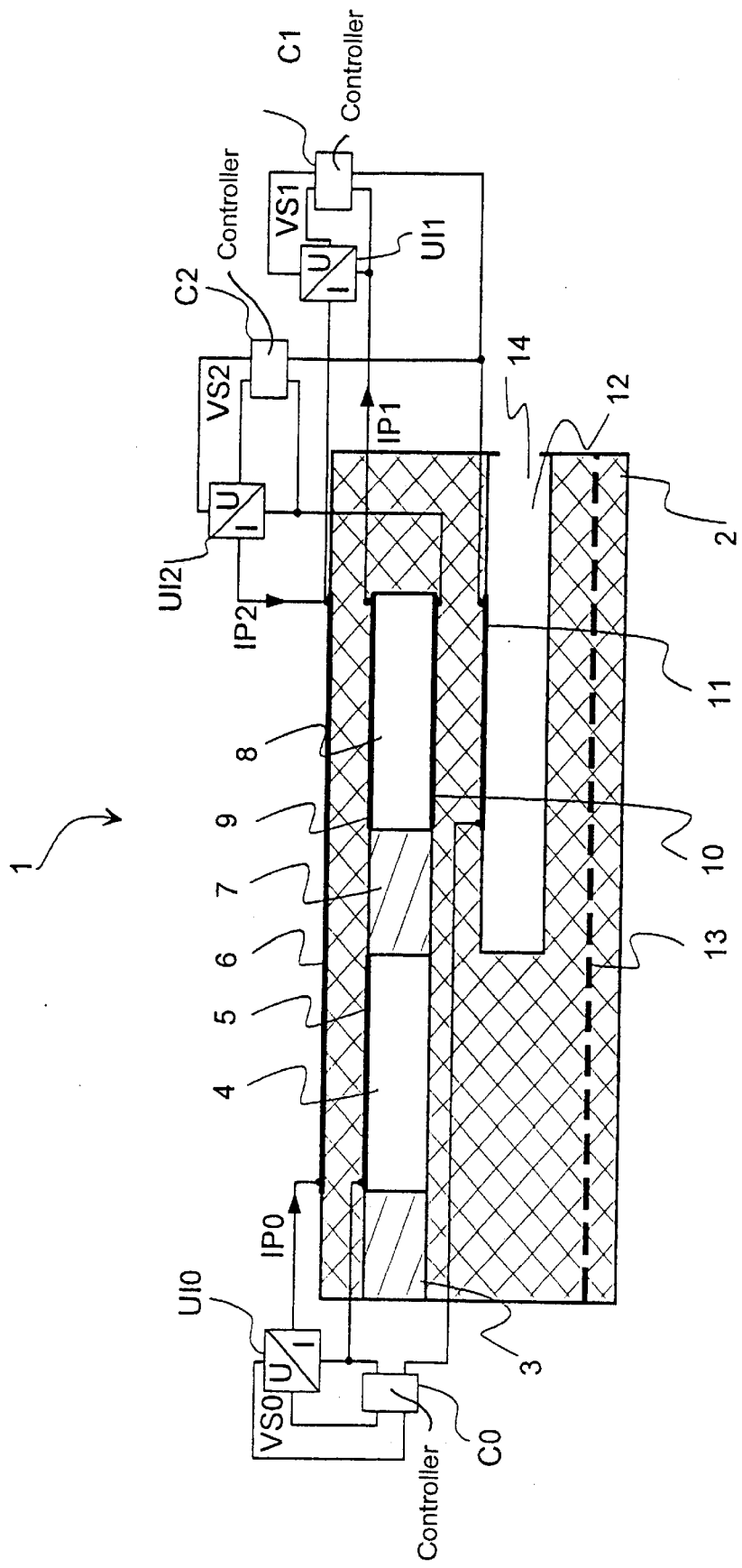
FIG. 2 is a sectional view through the NOx measurement sensor and a block diagram of the circuit.

The measurement sensor 24, 1 is illustrated in more detail in FIG. 2. The measurement sensor 1 which is composed of a solid-state electrolyte 2, in this case $ZrO_2$, picks up the exhaust gas which is to be measured, and whose NOx concentration is to be determined, via a diffusion barrier 3.

The exhaust gas diffuses through the diffusion barrier 3 into a first measurement cell 4. An oxygen content in the first measurement cell 4 is measured by tapping off a Nernst voltage between a first electrode 5 and a reference electrode 11 which is exposed to ambient air. In this case, the reference electrode 11 is disposed in an air duct 12, into which ambient air passes via an opening 14.

The Nernst voltage that is tapped off is fed to an 8-bit microcontroller that serves as a controller C0, which provides a setting voltage VS0 in a manner yet to be explained.

The setting voltage VS0 controls a voltage-controlled current source UI0, which drives a first oxygen ion pump current IP0 through the solid-state electrolyte 2 of the measurement sensor 1 between the first electrode 5 and an external electrode 6. At the same time, a predetermined oxygen concentration in the first measurement cell 4 is adjusted by the controller C0 by the setting voltage VS0. This concentration is measured via the Nernst voltage between the electrode 5 and the reference electrode 11, so that a control loop of the controller C0 is closed.

Figure 4:
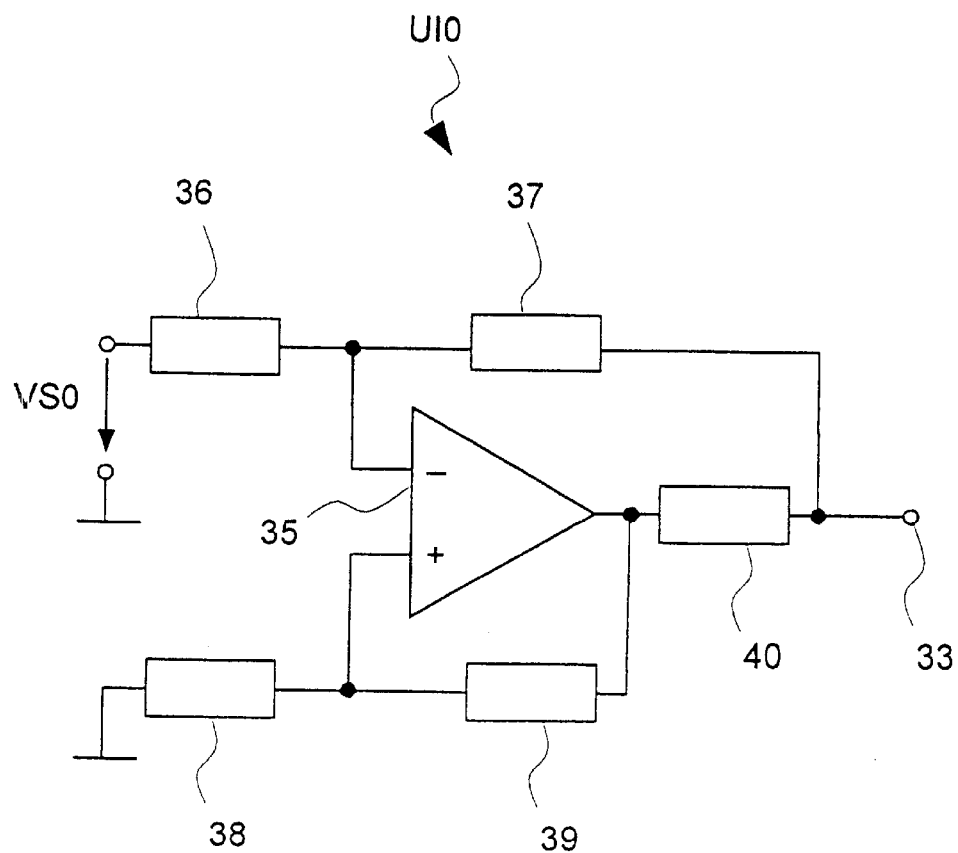
FIG. 4 is a circuit diagram of a voltage-controlled current source.

The voltage-controlled current source UI0 employed can be the circuit illustrated in FIG. 4. An operational amplifier 35 has the setting voltage VS0 applied to an inverting input via a resistor 36. The inverting input is also coupled back via a resistor 37 to an output of the operational amplifier 35. A non-inverting input of the operational amplifier 35 is connected via a resistor 38 to ground, and is coupled back via a resistor 39 to the output of the operational amplifier 35.

A resistor 40 is connected between the junctions of the non-inverting feedback branch and the inverting feedback branch. The current IP0 can be tapped off at an output 33 of the voltage-controlled current source UI0. This circuit has the advantage that the current IP0 is permanently defined by the setting voltage VS0, irrespective of an impedance of a load resistance, in this case of the pump circuit. The measurement of the current IP0 is not necessary, since VS0 and IP0 are linked to one another via the following equation:

$$IP0=VS0/R,$$

if R is a value of the resistor 40, and the resistors 36 through 39 all have the same resistance value, which is much higher than the value of the resistor 40.

If the inputs of the operational amplifier 25 are exchanged, the value of the resistor 40 must be much smaller than that of the resistors 36 through 39. The resistors 37 through 39 then have the same value, and the value of the resistor 40 is as large as that of a series circuit containing the resistors 36 and 39.

Instead of the voltage-controlled current source for grounded loads which is illustrated in FIG. 4, other operational amplifier circuits or other types of voltage-controlled current sources are of course possible.

The circuit configured described therefore establishes a predetermined oxygen concentration in the first measurement cell 4. A second measurement cell 8 is connected to the first measurement cell 4 via a further diffusion barrier 7. Through the diffusion barrier 7, the gas present in the first measurement cell 4 diffuses into the second measurement cell 8. In the second measurement cell 8, a second oxygen concentration is established via a circuit configuration. To this end, a second Nernst voltage is tapped off between a second electrode 9 and the reference electrode 11 and is fed to a controller C1, which, in a manner yet to be described, provides a second setting voltage VS1, with which a second voltage-controlled current source UI1 is driven. The circuit configuration for driving an oxygen ion pump current IP1 out of the second measurement cell 8 therefore corresponds to the circuit configuration for the first measurement cell 4. This also applies to the voltage-controlled current source described there: the voltage-controlled current source UI1 can correspond to the voltage-controlled current source UI0, for example it can be configured in accordance with FIG. 4. The circuit configuration drives the oxygen ion pump current IP1 in such a way that a predetermined oxygen concentration is established in the second measurement cell 8.

The oxygen concentration is selected such that NOx from the processes that proceed is not involved, in particular no decomposition takes place. The NOx is then pumped from the measurement electrode 10 to the external electrode 6 in a third oxygen ion pump current IP2 at the measurement electrode 10, which can be of a catalytic configuration. Since a residual oxygen content in the second measurement cell 8 has been lowered sufficiently, the oxygen ion pump current IP2 is essentially carried only by oxygen ions which originate from the decomposition of NOx at the measurement electrode 10. The pump current IP2 is therefore a measure of the NOx concentration in the second measurement cell 8 and therefore in the exhaust gas to be measured.

The pump current IP2, like the previous pump currents, is driven by a voltage-controlled current source UI2, whose setting voltage VS2 is predefined by a controller C2, which taps off the Nernst voltage between the measurement electrode and the reference electrode 11, and adjusts a predetermined Nernst voltage by predefining the setting voltage VS2.

Instead of measuring the pump current IP2, which represents the measure of the NOx concentration in the second measurement cell 8, the setting voltage VS2 is employed as a measurement signal, since the setting voltage VS2, as described, is directly linked to the driven pump current IP2. The complicated measurement of the pump current IP2 via a measurement resistor and suitable voltage tap is therefore unnecessary.

The controllers C0, C1, C2 employed in the circuit of FIG. 2 are preferably microcontrollers or a single microcontroller.

The setting voltages VS0, VS1, VS2 can be output at digital/analog ports of the microcontroller or microcontrollers. Preferably, however, use is made of the following circuit, illustrated in FIG. 3, in order to generate the setting voltage with the microcontroller.

Figure 3:
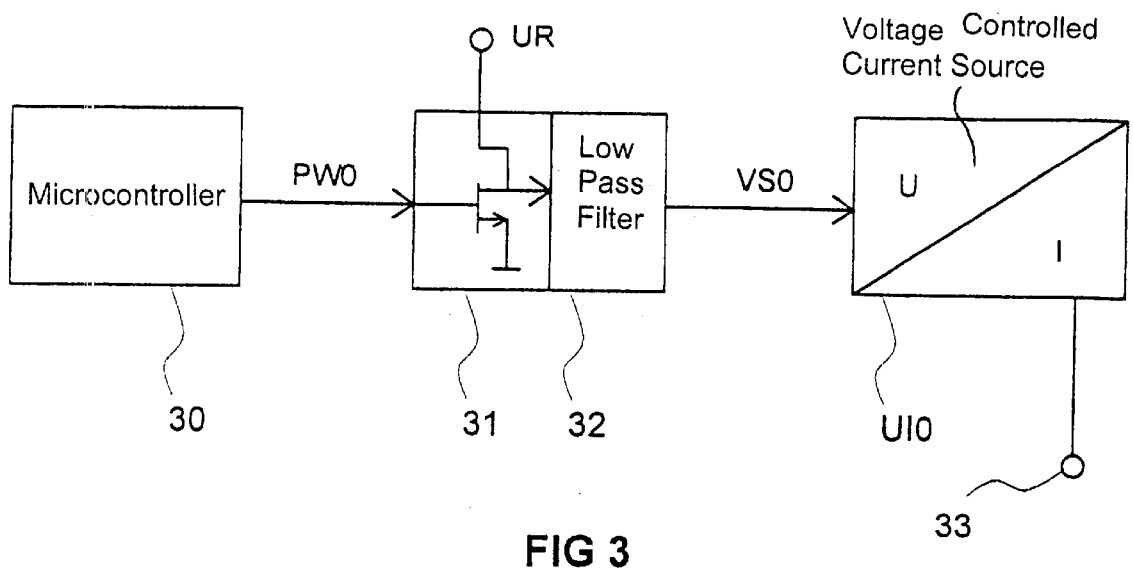
FIG. 3 is a block diagram illustrating a generation of a setting voltage.

FIG. 3 illustrates a microcontroller 30, which outputs a pulse-width-modulated signal PW0 at an output port. The signal PW0 is fed to a transistor circuit 31, to which a reference voltage UR is also applied. The transistor circuit 31 connects the reference voltage UR, in accordance with the pulse-width modulated signal PW0, to a low-pass filter 32 which, on account of its low-pass properties, generates from the signal the setting voltage VS0, a level of which is proportional to a pulse duty factor of the pulse-width modulated signal PW0. The setting voltage VS0 is employed to drive the voltage-controlled current source UI0, which makes the pump current IP0 available at its output 33. This scheme for generating the pump current IP0 is likewise used for the generation of the pump currents IP1 and IP2, it being possible for a single microcontroller 30 to provide the signals PW0, PW1 and PW2 at three output ports. Of course, three independent microcontrollers can also be employed.

I claim:

1. A circuit for a measurement sensor that registers an NOx concentration in a gas, the measurement sensor having an external electrode to be exposed to the gas to be measured, measurement cells including a first measurement cell and a second measurement cell connected to the first measurement cell, a measurement electrode disposed in the second measurement cell, a reference electrode exposed to ambient air, a solid-state electrolyte having the measurement cells disposed therein and the measurement electrode and the reference electrode making contact with the solid-state electrolyte, the circuit comprising:

a first circuit configuration for establishing in the first measurement cell an oxygen concentration differing from an oxygen concentration in the gas to be measured;

a second circuit configuration for establishing in the second measurement cell an oxygen concentration differing from the oxygen concentration in the first measurement cell; and a third circuit configuration for pumping oxygen ions formed from NOx out of the second measurement cell from the measurement electrode to the external electrode in a pump current, said third circuit configuration including:

a controller connected to the measurement electrode and the reference electrode and generating a setting voltage; and a voltage-controlled current source for driving the pump current and receiving the setting voltage generated by said controller, said controller tapping off a Nernst voltage between the measurement electrode and the reference electrode and regulating the setting voltage such that a predicted Nernst voltage is established, a value of the setting voltage being a measure of the pump current and consequently of the NOx concentration to be measured.

2. The circuit according to claim 1, wherein said first circuit configuration, includes:

a controller connected to the first electrode and the reference electrode and generating a setting voltage; and a voltage-controlled current source pumping a pump current of the oxygen ions from the first electrode to the external electrode, said voltage-controlled current source of said first circuit configuration receiving the setting voltage generated by said controller of said first circuit configuration, said controller of said first circuit configuration tapping off a further Nernst voltage between the first electrode and the reference electrode and regulates the setting voltage of the first circuit configuration such that a further predetermined Nernst voltage is established that is a measure of the oxygen concentration in the first measurement cell.

3. The circuit according to claim 1, wherein:

the measurement sensor has a further electrode in the second measurement cell;

said second circuit configuration having:

a controller connected to the further electrode and the reference electrode and generating a setting voltage; and a voltage-controlled current source pumping a pump current of the oxygen ions from the further electrode to the external electrode and receiving the setting voltage generated by said controller of said second circuit configuration, said controller of said second circuit configuration tapping off a further Nernst voltage between the further electrode and the reference electrode and regulates the setting voltage of the second circuit configuration such that a further predetermined Nernst voltage is established, which represents a measure of the oxygen concentration in the second measurement cell, said controller of said second circuit configuration adjusting the oxygen concentration such that essentially no decomposition of NOx takes place.

4. The circuit according to claim 1, wherein said controller of said third circuit configuration is a controller circuit including:

a microcontroller generating a pulse-width-modulated output signal with a pulse duty factor;

a transistor circuit receiving the pulse-width-modulated output signal and a reference voltage; and a low-pass filter disposed downstream of said transistor circuit, and generating the setting voltage of the third circuit configuration as a DC voltage proportional to the pulse duty factor of the pulse-width-modulated output signal.

5. The circuit according to claim 2, wherein said controller of said first circuit configuration is a controller circuit including:
   a microcontroller generating a pulse-width-modulated output signal with a pulse duty factor;
   a transistor circuit receiving the pulse-width-modulated output signal and a reference voltage; and
   a low-pass filter disposed downstream of said transistor circuit, and generating the setting voltage of the first circuit configuration as a DC voltage proportional to the pulse duty factor of the pulse-width-modulated output signal.

6. The circuit according to claim 3, wherein said controller of said second circuit configuration is a controller circuit including:
   a microcontroller generating a pulse-width-modulated output signal with a pulse duty factor;
   a transistor circuit receiving the pulse-width-modulated output signal and a reference voltage; and
   a low-pass filter disposed downstream of said transistor circuit, and generating the setting voltage of said second circuit configuration as a DC voltage proportional to the pulse duty factor of the pulse-width-modulated output signal.

7. The circuit according to claim 1, wherein said controller of said third circuit configuration is a microcontroller having an output and supplying the setting voltage of the third circuit configuration converted from a digital signal to an analog signal at said output.

8. The circuit according to claim 2, wherein said controller of said first circuit configuration is a microcontroller having an output and supplying the setting voltage of the first circuit configuration converted from a digital signal to an analog signal at said output.

9. The circuit according to claim 3, wherein said controller of said second circuit configuration is a microcontroller having an output and supplying the setting voltage of the second circuit configuration converted from a digital signal to an analog signal at said output.

10. The circuit according to claim 4, wherein said microcontroller is an 8-bit controller.

11. The circuit according to claim 5, wherein said microcontroller is an 8-bit controller.

12. The circuit according to claim 6, wherein said microcontroller is an 8-bit controller.

13. The circuit according to claim 7, wherein said microcontroller is an 8-bit controller.

14. The circuit according to claim 8, wherein said microcontroller is an 8-bit controller.

15. The circuit according to claim 9, wherein said microcontroller is an 8-bit controller.

16. The circuit according to claim 1, wherein said voltage-controlled current source of said third circuit configuration has:
   a current output;
   an operational amplifier with a non-inverting input, an inverting input and an output;
   a first resistor connected between a reference potential and said non-inverting input;
   a second resistor of equal magnitude to said first resistor connected between said non-inverting input and said output of said operational amplifier;
   a third resistor connected between said controller of said third configuration circuit and said inverting input such that said inverting input receives the setting voltage of the third configuration circuit;
   a fourth resistor connected between said inverting input and said output of said operational amplifier; and
   a fifth resistor connected between said output of said operational amplifier and said fourth resistor such that said fifth resistor is located between said current output of said voltage-controlled current source of said third configuration circuit and said output of said operational amplifier.

17. The circuit according to claim 2, wherein said voltage-controlled current source of said first circuit configuration has:
   a current output;
   an operational amplifier with a non-inverting input, an inverting input and an output;
   a first resistor connected between a reference potential and said non-inverting input;
   a second resistor of equal magnitude to said first resistor connected between said non-inverting input and said output of said operational amplifier;
   a third resistor connected between said controller of said first configuration circuit and said inverting input such that said inverting input receives the setting voltage of said first configuration circuit;
   a fourth resistor connected between said inverting input and said output of said operational amplifier; and
   a fifth resistor connected between said output of said operational amplifier and said fourth resistor such that said fifth resistor is located between said current output of said voltage-controlled current source of said first circuit configuration and said output of said operational amplifier.

18. The circuit according to claim 3, wherein said voltage-controlled current source of said second circuit configuration has:
   a current output;
   an operational amplifier with a non-inverting input, an inverting input and an output;
   a first resistor connected between a reference potential and said non-inverting input;
   a second resistor of equal magnitude to said first resistor connected between said non-inverting input and said output of said operational amplifier;
   a third resistor connected between said controller of said second configuration circuit and said inverting input such that said inverting input receives the setting voltage of said second configuration circuit;
   a fourth resistor connected between said inverting input and said output of said operational amplifier; and
   a fifth resistor connected between said output of said operational amplifier and said fourth resistor such that said fifth resistor is located between said current output of said voltage-controlled current source of said second configuration circuit and said output of said operational amplifier.

* * * * *